US00PP14326P29

(12) United States Plant Patent
van Rijn

(10) Patent No.: US PP14,326 P2
(45) Date of Patent: Dec. 2, 2003

(54) ANTHURIUM PLANT NAMED 'VR 172'

(50) Latin Name: *Anthurium andreanum*
Varietal Denomination: VR 172

(75) Inventor: Leonardus W. B. M. van Rijn, Schipluiden (NL)

(73) Assignee: RijnPlant B.V., Schipluiden (NL)

( * ) Notice: Subject to any disclaimer, the term of this patent is extended or adjusted under 35 U.S.C. 154(b) by 3 days.

(21) Appl. No.: 10/223,286

(22) Filed: Aug. 19, 2002

(51) Int. Cl.[7] ..... A01H 5/00

(52) U.S. Cl. ..... Plt./369

(58) Field of Search ..... Plt./369

*Primary Examiner*—Bruce R. Campell
*Assistant Examiner*—A Para
(74) *Attorney, Agent, or Firm*—C. A. Whealy

(57) ABSTRACT

A distinct cultivar of Anthurium plant named 'VR 172', characterized by its upright and outwardly spreading plant habit; freely clumping growth habit; durable dark green leaves; red-colored spathes with light red-colored spadices that are positioned above and beyond the foliage on strong and erect scapes; freely flowering habit; and good inflorescence longevity.

2 Drawing Sheets

BOTANICAL CLASSIFICATION/CULTIVAR DESIGNATION

*Anthurium andreanum*

BACKGROUND OF THE INVENTION

The present invention relates to a new and distinct cultivar of Anthurium plant, botanically known as *Anthurium andreanum*, and hereinafter referred to by the name 'VR 172'.

The new Anthurium is a product of a planned breeding program conducted by the Inventor in Schipluiden, The Netherlands. The objective of the program is to create and develop new compact, freely clumping and freely flowering Anthurium cultivars with strong roots, dark green leaves, attractive spathe color, and good inflorescence longevity.

The new Anthurium originated from a cross by the Inventor in November, 1997 of the *Anthurium andreanum* cultivar Orange Love, disclosed in U.S. Plant Pat. No. 11,117, as the female, or seed, parent with the *Anthurium andreanum* selection No. 97-15, not patented, as the male, or pollen, parent. The cultivar VR 172 was discovered and selected by the Inventor as a plant within the progeny of the stated cross in a controlled environment in Schipluiden, The Netherlands in 2000.

Asexual propagation of the new cultivar by meristem culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar VR 172. These characteristics in combination distinguish 'VR 172' as a new and distinct cultivar:

1. Upright and outwardly spreading plant habit.
2. Freely clumping growth habit.
3. Durable, small, dark green leaves.
4. Red-colored spathes with light red-colored spadices that are positioned above and beyond the foliage on strong and erect scapes.
5. Freely flowering habit.
6. Good inflorescence longevity.

Plants of the new Anthurium can be compared to plants of the female parent, the cultivar Orange Love. In side-by-side comparisons conducted in Schipluiden, The Netherlands, plants of the new Anthurium differed from plants of the cultivar Orange Love in the following characteristics:

1. Plants of the new Anthurium had slightly smaller and more durable leaves than plants of the cultivar Orange Love.
2. Plants of the new Anthurium had larger and more durable spathes than plants of the cultivar Orange Love.

Plants of the new Anthurium can be compared to plants of the male parent, the selection 97-15. In side-by-side comparisons conducted in Schipluiden, The Netherlands, plants of the new Anthurium differed from plants of the selection 97-15 in the following characteristics:

1. Plants of the new Anthurium were more compact than plants of the selection 97-15.
2. Plants of the new Anthurium had smaller leaves and spathes than plants of the selection 97-15.
3. Plants of the new Anthurium had red-colored spathes whereas plants of the selection 97-15 had white-colored spathes.

Plants of the new Anthurium can also be compared to plants of the cultivar Baby Red, disclosed in U.S. Plant Pat. No. 11,468. In side-by-side comparisons conducted in Schipluiden, The Netherlands, plants of the new Anthurium differed from plants of the cultivar Baby Red in the following characteristics:

1. Plants of the new Anthurium had slightly larger leaves than plants of the cultivar Baby Red.
2. Plants of the new Anthurium had larger spathes than plants of the cultivar Baby Red.
3. Plants of the new Anthurium and the cultivar Baby Red differed in spathe color.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a side perspective view of a typical flowering plant of the cultivar VR 172.

The photograph at the top of the second sheet comprises a close-up view of a typical inflorescence of 'VR 172'.

The photograph at the bottom of the second sheet comprises a close-up view of the upper surface of a typical mature leaf of 'VR 172'.

DETAILED BOTANICAL DESCRIPTION

In the following description, color references are made to The Royal Horticultural Society Colour Chart except where general terms of ordinary dictionary significance are used. The aforementioned photographs and the following observations and measurements describe two-year old plants grown in containers in Schipluiden, The Netherlands, in a glass greenhouse with an average day temperature of 25° C. and an average night temperature of 19° C.

Botanical classification: *Anthurium andreanum* cultivar VR 172.

Parentage:

*Female parent.*—*Anthurium andreanum* cultivar Orange Love, disclosed in U.S. Plant Pat. No. 11,117.

*Male parent.*—*Anthurium andreanum* selection number 97-15, not patented.

Propagation:

*Method.*—By meristem culture.

*Time to develop roots on a meristem-cultured plant.*—Summer: About 70 days at 24° C. Winter: About 84 days at 21° C.

*Root description.*—Strong fleshy roots.

Plant description:

*Plant shape.*—Upright and outwardly spreading plant habit, inverted triangle, symmetrical.

*Growth habit.*—Freely clumping, bushy and dense growth habit. Appropriate for 9 to 20-cm containers. Vigorous.

*Plant height.*—About 60 to 70 cm.

*Plant diameter or spread.*—About 95 cm.

*Crop time.*—About 10 months are usually required from planting of young plants to finished plants in a 17-cm container.

*Foliage description.*—Quantity per plant: More than 100. Length: About 9 to 15 cm. Width: About 9 to 10 cm. Shape: Deltoid. Apex: Apiculate to cuspidate. Base: Cordate. Margin: Entire, slightly undulate. Texture, upper and lower surfaces: Leather; glabrous, smooth. Venation pattern: Pinnate. Color: Young leaves, upper surface: 146A. Young leaves, lower surface: 148A. Mature leaves, upper surface: 147A. Mature leaves, lower surface: 144A to 146B. Venation, upper surface: 144A. Venation, lower surface: 146D. Petiole: Length: About 25 to 30 cm. Color: 146D. Geniculum length: About 1 to 3 cm. Geniculum color: 144A.

Inflorescence description:

*Inflorescence arrangement.*—Spathes with spadices held above and beyond the foliage. Flowering structures arise from leaf axils. Freely and continuous flowering year-round; typically more than 25 inflorescences per plant at one time.

*Inflorescence longevity.*—Inflorescences last about six weeks under winter conditions and about three months under summer conditions; persistent.

*Spathe.*—Length: About 7 to 10 cm. Width: About 6.5 to 9.5 cm. Shape: Broadly cordate. Apex: Apiculate, recurved. Base: Obtuse. Margin: Entire. Texture, upper and lower surfaces: Leathery; glabrous, smooth. Color: When opening, front and back surfaces: 46C. Fully developed, front surface: 46C; becoming closer to 47A with subsequent development. Fully opened, back surface: 51B.

*Spadix.*—Length: About 4 to 6.5 cm. Diameter: About 7 to 8 mm. Shape: Columnar. Cross section: Rounded. Longitudinal axis: Weakly curved. Color: Close to 48C; becoming green, 146B, with subsequent development.

*Flowers.*—Quantity per spadix: Numerous, about 150. Shape: Rounded. Diameter: About 1 mm, maximum.

*Reproductive organs.*—Androecium: Pollen color: 158A. Gynoecium: Stigma shape: Ovoid.

*Scape.*—Length: About 30 to 35 cm. Aspect: Strong and erect. Color: 144A to 146A; overlain with anthocyanin, 178B, towards the apex.

*Seed/fruit.*—Seed/fruit development on plants of the new Anthurium has not been observed.

Disease/pest resistance: Under commercial conditions, plants of the new Anthurium have not been observed to be resistant to pathogens or pests common to Anthurium.

It is claimed:

1. A new and distinct cultivar of Anthurium plant named 'VR 172', as illustrated and described.

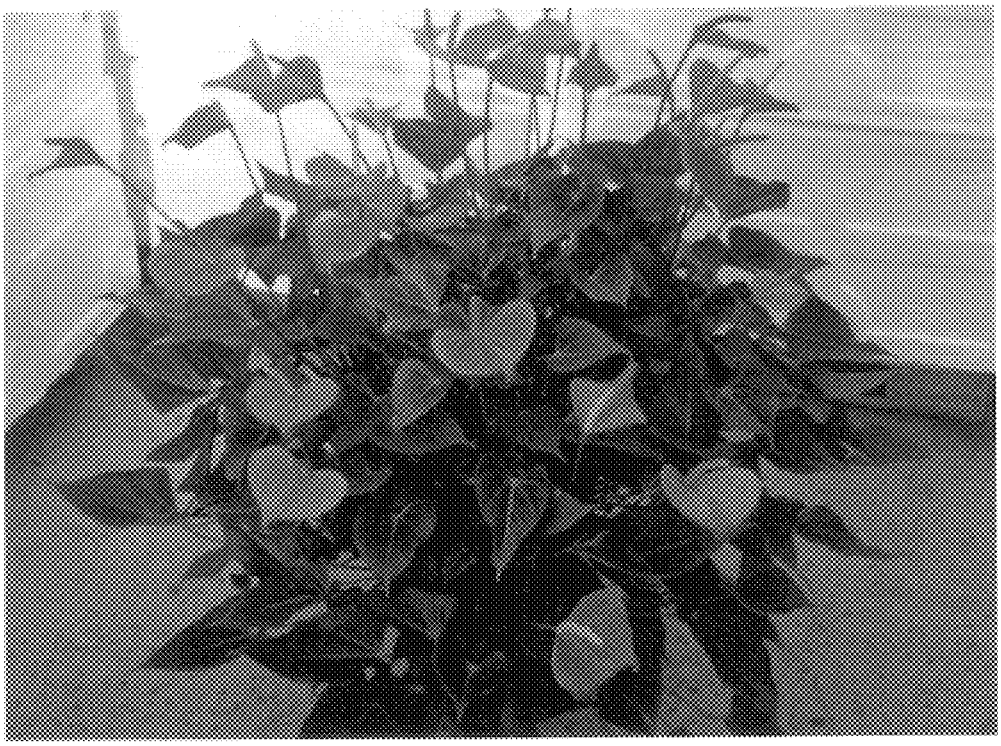

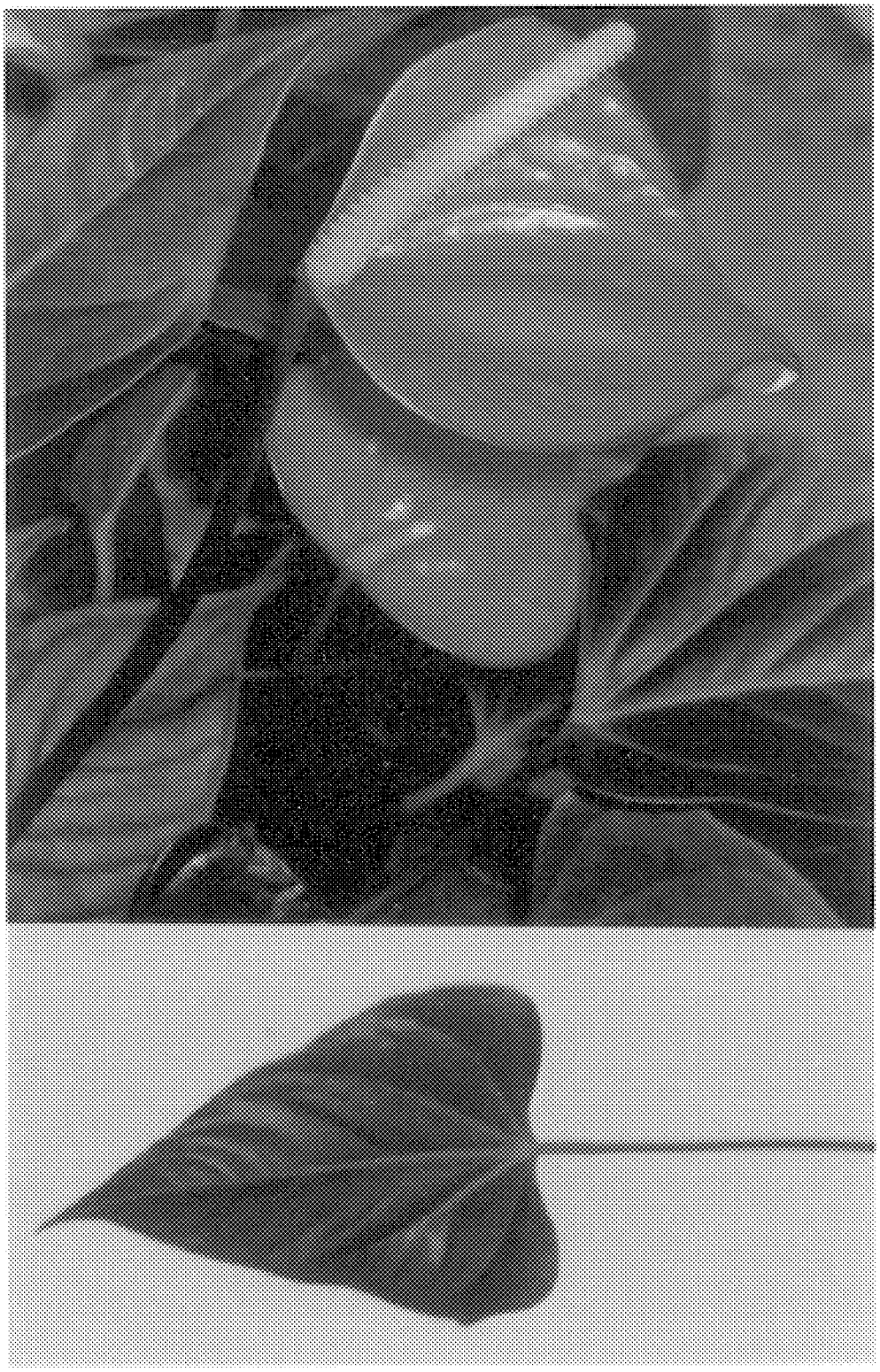

* * * * *